US006953476B1

(12) United States Patent
Shalev

(10) Patent No.: US 6,953,476 B1
(45) Date of Patent: Oct. 11, 2005

(54) DEVICE AND METHOD FOR TREATING ISCHEMIC HEART DISEASE

(75) Inventor: Ilan Shalev, Givatayim (IL)

(73) Assignee: Neovasc Medical Ltd., Or Yehuda (IL)

( * ) Notice: Subject to any disclaimer, the term of this patent is extended or adjusted under 35 U.S.C. 154(b) by 0 days.

(21) Appl. No.: 09/534,968

(22) Filed: Mar. 27, 2000

(51) Int. Cl.⁷ ............................................... A61F 2/06
(52) U.S. Cl. ................................................. 623/1.15
(58) Field of Search .................. 623/1.15, 1.1, 623/1.11–1.14, 1.16, 1.18, 1.2, 1.23, 1.24–1.29, 623/1.3, 1.34, 1.36, 1.5–1.53; 606/200

(56) References Cited

U.S. PATENT DOCUMENTS

| | | |
|---|---|---|
| 3,620,218 A | 11/1971 | Shmitt |
| 4,106,129 A | 8/1978 | Carpentier et al. |
| 4,297,749 A | 11/1981 | Davis et al. |
| 4,494,531 A | 1/1985 | Gianturco |
| 4,501,263 A | 2/1985 | Harbuck |
| 4,601,718 A | 7/1986 | Possis et al. |
| 4,727,873 A | 3/1988 | Mobin-Uddin |
| 4,893,623 A | 1/1990 | Rosenbluth |
| 4,994,066 A | 2/1991 | Voss |
| 5,007,926 A | 4/1991 | Derbyshire |
| 5,026,377 A | 6/1991 | Burton et al. |
| 5,064,435 A * | 11/1991 | Porter ........................ 623/23.7 |
| 5,078,736 A | 1/1992 | Behl |
| 5,129,902 A | 7/1992 | Goble et al. |
| 5,201,757 A | 4/1993 | Heyn et al. |
| 5,246,445 A | 9/1993 | Yachia et al. |
| 5,282,823 A | 2/1994 | Schwartz et al. |
| 5,304,194 A | 4/1994 | Chee et al. |
| 5,330,482 A | 7/1994 | Gibbs et al. |
| 5,342,348 A | 8/1994 | Kaplan |
| 5,354,309 A | 10/1994 | Schnepp-Pesch et al. |
| 5,375,612 A | 12/1994 | Cottenceau et al. |
| 5,382,261 A | 1/1995 | Palmaz |
| 5,397,351 A | 3/1995 | Pavcnik et al. |
| 5,409,019 A | 4/1995 | Wilk |
| 5,476,506 A * | 12/1995 | Lunn .......................... 623/1.13 |
| 5,514,176 A | 5/1996 | Bosley, Jr. et al. |
| 5,554,185 A | 9/1996 | Block et al. |
| 5,575,818 A * | 11/1996 | Pinchuk ...................... 606/195 |
| 5,609,627 A * | 3/1997 | Goicoechea et al. ........ 128/898 |
| 5,618,301 A | 4/1997 | Hauenstein et al. |
| 5,645,551 A | 7/1997 | Green et al. |
| 5,653,744 A | 8/1997 | Khouri |
| 5,655,548 A | 8/1997 | Nelson et al. |
| 5,662,713 A | 9/1997 | Andersen et al. |

(Continued)

FOREIGN PATENT DOCUMENTS

DE    26 13 575    10/1983

(Continued)

OTHER PUBLICATIONS

Brofman, B.L.; "Long Term Influence of the Beck Operation for Coronary Heart Disease;" Aug. 1960; American Journal of Cardiology; pp. 259–270.

(Continued)

*Primary Examiner*—(Jackie) Tan-Uyen T. Ho
(74) *Attorney, Agent, or Firm*—Fenster & Company

(57) ABSTRACT

A narrowing intraluminal stent is disclosed and comprises a hollow body and a flow passage therethrough, the hollow body designed for intraluminal placement and having at least one portion of an inner cross sectional dimension smaller than the cross sectional dimension of the lumen, so as to artificially narrow a passage through the body lumen. A method of artificially narrowing a passage through a body lumen using the stent is also disclosed.

19 Claims, 6 Drawing Sheets

U.S. PATENT DOCUMENTS

| | | | |
|---|---|---|---|
| 5,683,411 A * | 11/1997 | Kavteladze et al. | 606/200 |
| 5,695,504 A | 12/1997 | Gifford, III et al. | |
| 5,709,335 A | 1/1998 | Heck | |
| 5,713,908 A | 2/1998 | Jameel et al. | |
| 5,716,393 A | 2/1998 | Lindenberg et al. | |
| 5,732,872 A | 3/1998 | Bolduc et al. | |
| 5,741,333 A * | 4/1998 | Frid | 623/1.18 |
| 5,755,769 A * | 5/1998 | Richard et al. | 623/1.2 |
| 5,755,779 A * | 5/1998 | Horiguchi | 606/157 |
| 5,772,668 A | 6/1998 | Summers et al. | |
| 5,782,844 A | 7/1998 | Yoon et al. | |
| 5,782,905 A * | 7/1998 | Richter | 623/1.1 |
| 5,797,930 A | 8/1998 | Ovil | |
| 5,810,850 A | 9/1998 | Hathaway et al. | |
| 5,843,117 A | 12/1998 | Alt et al. | |
| 5,873,906 A | 2/1999 | Lau et al. | |
| 5,876,418 A | 3/1999 | KarlheinzHauenstein et al. | |
| 5,876,445 A | 3/1999 | Andersen et al. | |
| 5,897,588 A | 4/1999 | Hull et al. | |
| 5,925,063 A | 7/1999 | Khosravi | |
| 6,015,432 A | 1/2000 | Rakos et al. | |
| 6,053,873 A | 4/2000 | Govari et al. | |
| 6,070,589 A * | 6/2000 | Keith et al. | 128/898 |
| 6,071,292 A | 6/2000 | Makower et al. | |
| 6,110,198 A * | 8/2000 | Fogarty et al. | 128/898 |
| 6,120,534 A * | 9/2000 | Ruiz | 606/194 |
| 6,159,156 A | 12/2000 | Van Bockel et al. | |
| 6,168,614 B1 | 1/2001 | Andersen et al. | |
| 6,254,627 B1 * | 7/2001 | Freidberg | 606/195 |
| 6,293,968 B1 | 9/2001 | Taheri | |
| 6,296,603 B1 * | 10/2001 | Turnlund et al. | 600/3 |
| 6,325,813 B1 | 12/2001 | Hektner | |
| 6,348,066 B1 * | 2/2002 | Pinchuk et al. | 606/198 |
| 6,579,306 B1 * | 6/2003 | Voelker et al. | 623/1.11 |
| 2001/0021872 A1 | 9/2001 | Bailey et al. | |

FOREIGN PATENT DOCUMENTS

| | | |
|---|---|---|
| DE | 91 01 344 | 7/1991 |
| DE | 195 09 464 | 6/1996 |
| EP | 0 556 850 | 8/1983 |
| EP | 0 587 197 | 3/1994 |
| EP | 0 779 062 | 6/1997 |
| WO | WO 92/06734 | 4/1992 |
| WO | WO 93/08767 | 5/1993 |
| WO | WO 98/46115 | 10/1998 |
| WO | WO 99/34731 | 7/1999 |
| WO | WO 99/65418 | 12/1999 |
| WO | WO 00/32092 | 6/2000 |

OTHER PUBLICATIONS

Beck, C.S. et al.; "The Surgical Management of Coronary Artery Disease: Background,Rationale,Clinical Experience;" Dec. 1956; American College of Physicians in Annals of Internal Medicine; vol. 45, No. 6; pp. 975-986.

Faxon,M. D. et al.; "Coronary Sinus Occlusion Pressure and Its Relation to Intracardiac Pressure;" Sep. 1, 1985; The American Journal of Cardiology; vol. 56; pp. 457-460.

Sandler, G. et al.; "The Beck Operation in the Treatment of Angina Pectoris;"Thorax; vol. 32; No. 34.

Wising, P.J.; "The Beck-I Operation for Angina Pectoris;" 1963; Acta Medica Scandinavica; vol. 174; Fasc. 1; pp. 93-97.

Zalewski,A. et al.; "Myocardial Protection Via Coronary Sinus Interventions:Superior Effects of Arterialization Compared with Intermittent Occlusion;" Jun. 1985; Laboratory Investigation-Myocardial Ischemia; vol. 71; No. 6; pp. 1215-1222.

Beck, C.S. et al.; "Operation for Coronary Artery Disease;" Nov. 27, 1954; J.A.M.A.; vol. 156; No. 13; pp. 1226-1233.

Beck, C.S. et al.; "Scientific Basis for the Surgical Treatment of Coronary Artey Disease;" Nov. 26, 1955; J.A.M.A. vol. 159; No. 13; pp. 1264-1271.

Beck, C.S. et al.; "Some New Concepts of Coronary Heart Disease. Results after Surgical Operation;" Dec. 20, 1958; J.A.M.A.; vol. 168; No. 16; pp. 2110-2117.

Beck, C.S. et al.; "The Coronary Patient Wants Better Treatment;" Jan. 1961; Medical Times; NY; vol. 89; No. 1; pp. 17-26.

Braunwald,E.; "Heart Disease: A textbook of Cardiovascular Medicine;" 1997; 5th Edition; W.B. Saunders Company; Chapter 36; pp. 1168-1169.

Gross,L. et al.; "ExperimentalAttempts to Increase the Blood Supply to the Dog's Heart by Means of Coronary Sinus Occlusion;" Jan. 1937; Journal Exper.Med.; vol. 65; pp. 91-108 and plates 4-5.

Robertson,H.F.; "The Recstablishment of Cardiac Cirrulation during Proogressive Coronary Occlusion;" 1935; The American Heart Journal; vol. 10; pp. 533-541.

* cited by examiner

DEVICE AND METHOD FOR TREATING ISCHEMIC HEART DISEASE

FIELD AND BACKGROUND OF THE INVENTION

The present invention relates to a device and method for treating ischemic heart disease and, more particularly, to a coronary sinus stent and to surgical methods for implanting same. Specifically, the present invention involves implantation of the stent in the coronary sinus as a means of treating patients suffering from, for example, diffuse coronary artery disease, especially in cases where conventional balloon catheterization, bypass surgery and drugs are infeasible or ineffective treatment methods.

Blood arrives at the heart muscle via coronary arteries which begin as vessels with a diameter of several millimeters and branch progressively to smaller and smaller vessels in order to supply all the cells of the heart muscle. Blood arriving at the heart carries oxygen and nutrients which are exchanged for carbon dioxide and other wastes produced by cellular respiration. The carbon dioxide carrying blood leaves the heart muscle via a system of coronary veins which begin as small vessels and progressively merge into larger vessels. As in other organs, the veins are approximately parallel to the arteries, although the blood flow therein is in the opposite direction. The coronary veins terminate in a reservoir referred to as the coronary sinus, which, in turn, drains into the right atrium where it mixes with venous blood from peripheral organs. Venous blood is pumped from the right atrium into the pulmonary arteries which perfuse the lung and facilitate an exchange of gases, with carbon dioxide being replaced with oxygen.

In cases where the supply of blood flowing to the heart muscle via the coronary arteries is insufficient, oxygenation of the muscle tissue of the heart is reduced, producing a condition known as cardiac ischemia. Ischemia can result in atrophy and or necrosis of tissue. In the case of cardiac ischemia, this atrophy or necrosis reduces heart function and adversely affects the blood supply to the remainder of the body. Patients suffering from cardiac ischemia typically suffer from chest pains and difficulty in breathing. Cardiac ischemia may precipitate a heart attack in some cases.

Cardiac ischemia is most often caused by atherosclerosis or other conditions which block one or more coronary arteries. Current treatment options include balloon catheterization, bypass surgery and treatment with drugs. Balloon catheterization and bypass surgery are only feasible options if the coronary artery blockage exists in a small number of discrete locations, usually in fairly large blood vessels.

Balloon catheterization involves insertion of a catheter with an inflatable tip via a peripheral blood vessel into the affected coronary artery. The procedure is performed with the aid of a visualization (imaging) device (e.g., ultrasound, X-ray, fluoroscopy) which shows the catheter tip and the coronary artery occlusion. When the tip is in proximity to the occlusion, it is inflated, thereby widening the artery and releasing the occlusion. In cases, the balloon catheter serves for placing a stent within the artery and to extend or erect the stent to its service dimensions in a process known as stent catheterization. These procedures are often preferred by patients and doctors because it is relatively non-invasive.

Bypass surgery is an invasive procedure which involves opening the thoracic cavity and implanting a tube so as to replace or bypass an occluded portion of the coronary artery. The tube may be either artificial, or a peripheral blood vessel derived from the patient. While this method has proven efficacy, it has all of the disadvantages inherent in invasive surgery, e.g., post-surgical infection, complications with anesthesia, relatively long recovery time and high cost.

Patients with cardiac ischemia caused by blockage of many small vessels are not candidates for balloon catheterization or bypass surgery and are currently treatable only with drugs. These drugs include, for example, nitrates, β-blockers and calcium channel blockers. Unfortunately, patients treated with drugs often continue to have difficulty performing daily activities, suffer from shortness of breath and chest pains.

It has long been known that reducing the flow of blood exiting the coronary sinus can have beneficial effects on cardiac ischemia (Gross L. Blum L., Silverman G. J Exper. Med. (1937) 85:91, 1937; Robertson H. H. (1935) Am Heart. J. 10:533; Beck C. S., Leighninger D. S. (1954) Am. Heart J. 156:1226; Beck C. S., Leighninger D. S. (1955) Am. Heart J. 159:1264; Beck C. S., Leighninger D. S. (1961) Med. Tms. (NY) 89:17; Beck C. S., Leighninger D. S., Brofman B. L., Bond J. F. (1958) J. Amer. Med. Ass. 168:2110; Sandler G., Slesser B. V., Lawson C. W. (1967) Thorax 22:34). It is believed that reducing the flow of blood exiting the coronary sinus increases the blood pressure in the coronary arteries, thereby inducing the formation of new blood vessels, a process known as angiogenesis. The prior art procedure of reducing the flow of blood exiting the coronary sinus involves placement of a narrowing ring external to the coronary sinus, so as to narrow its inner diameter and thereby restrict blood flow therethrough. This procedure, however, is an open chest (thoracic) procedure, and therefore suffers all the limitations associated with such procedures, including, but not limited to, post-surgical infection, complications with anesthesia, relatively long recovery time and high cost. However, the prior art fails to teach minimal invasive means of reducing the flow of blood exiting the coronary sinus without thoracic surgery.

There is thus a widely recognized need for, and it would be highly advantageous to have, a device and method for reducing the flow of blood exiting the coronary sinus without thoracic surgery as a means of treating or preventing cardiac ischemia caused by, for example, diffuse coronary artery disease.

SUMMARY OF THE INVENTION

According to one aspect of the present invention there is provided a narrowing intraluminal stent for placement in a body lumen having a cross sectional dimension, the narrowing intraluminal stent comprising a hollow body having a first end, a second end, and a flow passage being defined therethrough from the first end to the second end, the hollow body being designed for intraluminal placement in the body lumen and having at least one portion of an inner cross sectional dimension smaller than the cross sectional dimension of the body lumen, so as to artificially narrow a passage through the body lumen.

According to another aspect of the present invention there is provided a method of artificially narrowing a passage through a body lumen having a cross sectional dimension, the method comprising the step of implanting a narrowing intraluminal stent in the body lumen, thereby artificially narrowing the passage through a body lumen.

According to yet another aspect of the present invention there is provided a method of initiating or accelerating angiogenesis in order to treat or prevent ischemia, the method comprising the step of artificially narrowing a passage through a blood vessel having a cross sectional dimension by implanting a narrowing intraluminal stent therein, thereby reducing a flow of blood therethrough, creating back pressure and initiating or accelerating angiogenesis upstream thereto.

According to further features in preferred embodiments of the invention described below, the stent is constructed of a biologically inert material.

According to still further features in the described preferred embodiments, the stent is coated with a biologically inert material.

According to further features in preferred embodiments of the invention described below, the biologically inert material is selected from the group consisting of stainless steel, nitinol and biocompatible plastic material.

According to still further features in the described preferred embodiments, the hollow body further includes at least one expandable portion for affixing the narrowing intraluminal stent in the body lumen.

According to still further features in the described preferred embodiments, the lumen is a coronary sinus and the stent is configured for placement therein so as to decrease a flow of blood therethrough.

According to still further features in the described preferred embodiments, the decrease in flow of blood through the coronary sinus is sufficient so as to cause coronary angiogenesis.

According to still further features in the described preferred embodiments, the inner cross sectional dimension of the hollow body is greater than 7 mm$^2$ and less than 28 mm$^2$.

According to still further features in the described preferred embodiments, the length of the hollow body, from the first end to the second end, is greater than 20 mm and less than 50 mm.

According to still further features in the described preferred embodiments, an aspect ratio defined by an inner cross sectional diameter of the hollow body divided by a length of the hollow body from the first end to the second end is greater than 0.1 and less than 0.2.

According to still further features in the described preferred embodiments, a ratio defined by a narrowest inner cross sectional diameter of the hollow body divided by a length of the hollow body from the first end to the second end is greater than 0.1 and less than 0.2.

According to still further features in the described preferred embodiments, the at least one expandable portion expands as a result of an occurrence selected from the group consisting of (i) application of a force which expands the at least one expandable portion; and (ii) removal of a force which contracts the at least one expandable portion.

According to still further features in the described preferred embodiments, the force which expands the at least one expandable portion is suppliable by an inflatable balloon of a catheter receivable within the hollow body of the stent.

According to still further features in the described preferred embodiments, the affixing of the narrowing intraluminal stent in the body lumen occurs as a result of a cause selected from the group consisting of (i) a physical contact between a portion of the narrowing intraluminal stent and an inner surface of the body lumen; and (ii) a biological process occurring in cells of an inner surface of the body lumen as a result of a presence therein of the narrowing intraluminal stent.

According to still further features in the described preferred embodiments, the hollow body further includes at least two expandable portions for affixing the narrowing intraluminal stent in the body lumen.

According to still further features in the described preferred embodiments, an integrity of the at least one expandable portion is preserved during a transition from elasticity to plasticity.

According to still further features in the described preferred embodiments, the at least one expandable portion comprises an expandable grid.

According to still further features in the described preferred embodiments, the step of implanting the narrowing intraluminal stent in the body lumen is effected with a catheter.

According to still further features in the described preferred embodiments, guiding the catheter to the lumen is effected under imaging.

According to still further features in the described preferred embodiments, the step of implanting the narrowing intraluminal stent in the body lumen and the step of expanding the at least one expandable portion are effected with a balloon catheter.

According to still further features in the described preferred embodiments, guiding the balloon catheter to the lumen is effected under imaging.

According to still further features in the described preferred embodiments, the imaging is accomplished by a method selected from the group consisting of computer assisted tomography (CT), magnetic resonance imaging (MRI), proton emission tomography (PET), ultrasonography, three dimensional ultrasonography, fluoroscopy, electrophysiological imaging, X-ray imagery and echocardiography.

The present invention successfully addresses the shortcomings of the presently known configurations by providing a device and method for treating or preventing cardiac ischemia caused by, for example, diffuse coronary artery disease which does not require thoracic surgery.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
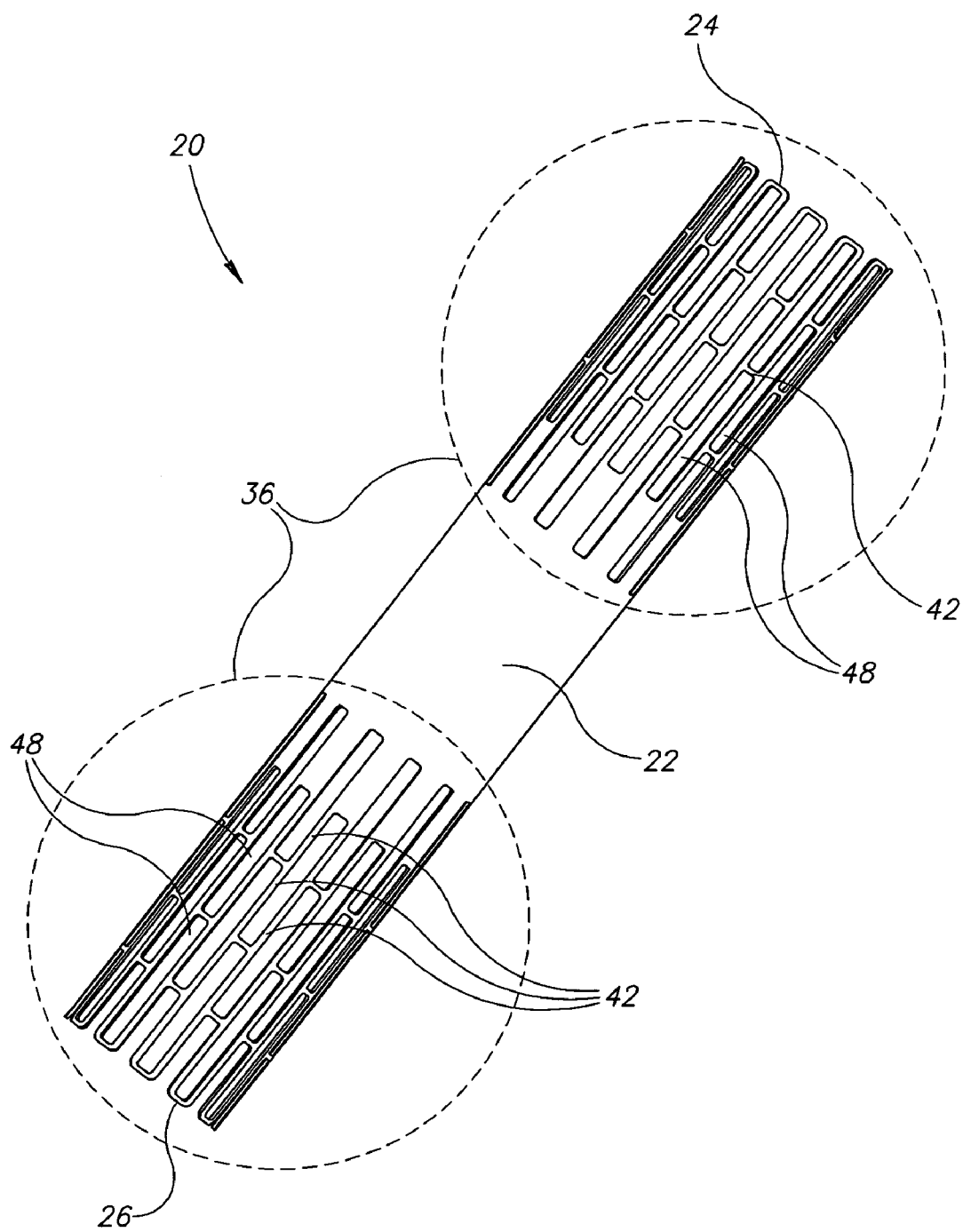
FIG. 1 is a perspective view of one embodiment of a core construction of the stent of the present invention shown in a non-expanded position.

The present invention is of a device and method which can be used in treating or preventing ischemic heart disease and, more particularly, to a coronary sinus narrowing stent and to surgical methods for implanting same. Specifically, the present invention involves implantation of the stent in the coronary sinus as a means of treating patients suffering from, for example, diffuse coronary artery disease, especially in cases where conventional balloon catheterization, bypass surgery and drugs are infeasible or ineffective treatment methods.

The principles and operation of a device and methods which can be used for treating or preventing ischemic heart disease according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 1–6 illustrate a narrowing intraluminal stent for placement in a body lumen 28, which stent is referred to hereinbelow as stent 20. Stent 20 includes a hollow body 22. Body 22 has a first end 24, a second end 26, and a flow passage 30 (see FIG. 6) defined therethrough, from first end 24 to second end 26. Hollow body 22 is designed for intraluminal placement in the body lumen 28 and has at least one portion 32 of an inner cross sectional dimension smaller than a cross sectional dimension 34 of body lumen 28, so as to artificially narrow a passage through body lumen 28.

Accordingly, the present invention is also provides a method of artificially narrowing a passage through body lumen 28 having a cross sectional dimension 34. The method includes the step of implanting stent in body lumen 28, thereby artificially narrowing the passage through body lumen 28. Such placement, when in a blood vessel, is used to initiate or accelerate angiogenesis in order, for example, to treat or prevent ischemia by reducing a flow of blood through the blood vessel, creating back pressure and initiating or accelerating angiogenesis upstream thereto.

In order to facilitate safe use of stent 20, and to allow practice of the methods described hereinabove, stent 20 is preferably constructed of, or it is coated with, a biologically inert material. Biologically inert materials suited for use in constructing or coating stent 20 include, but are not necessarily limited to, stainless steel, nitinol and biocompatible plastic material.

Figure 2:
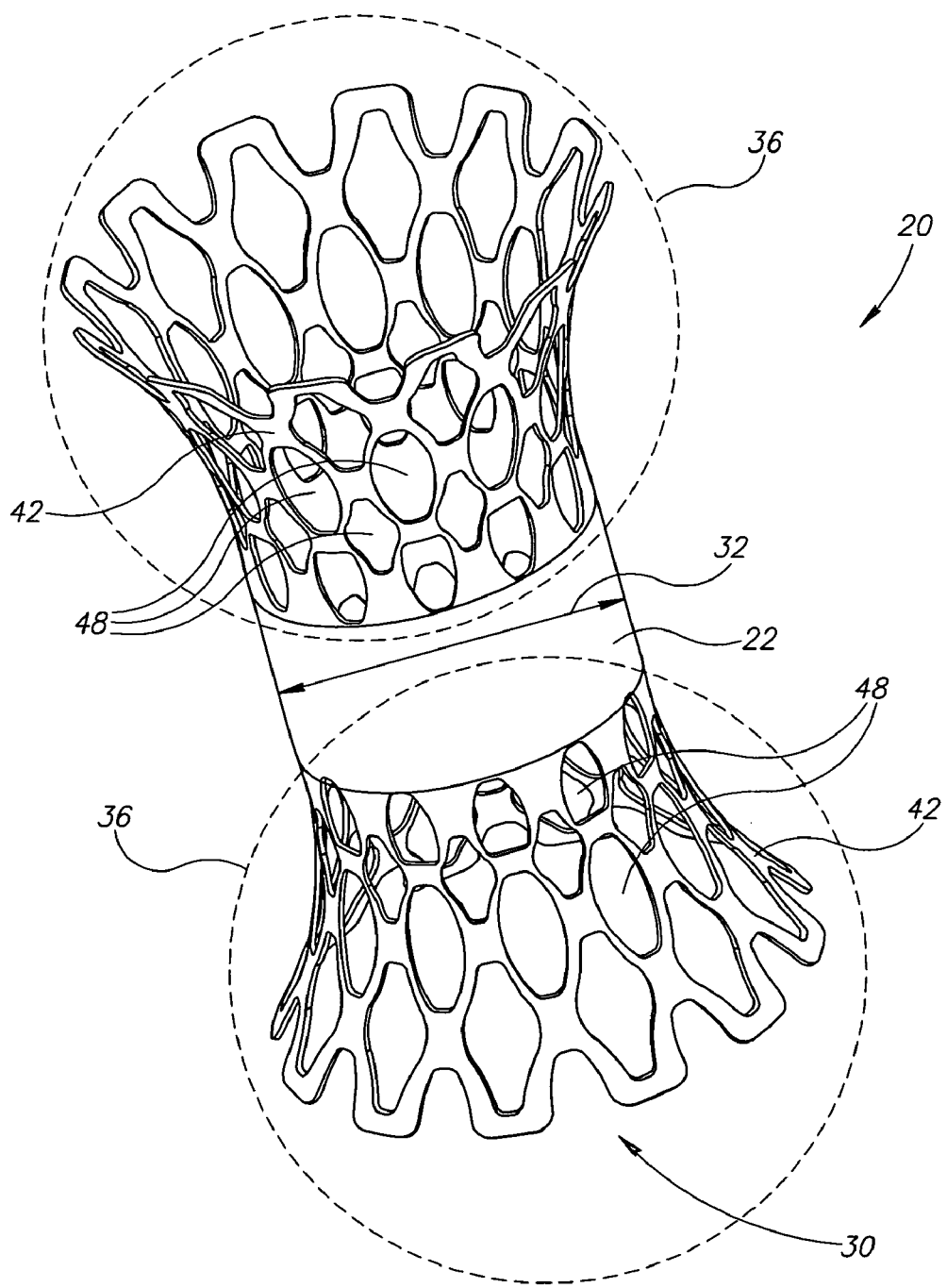
FIG. 2 is a perspective view of the same embodiment of the core construction of the stent of the present invention in an expanded position.
Figure 3A:
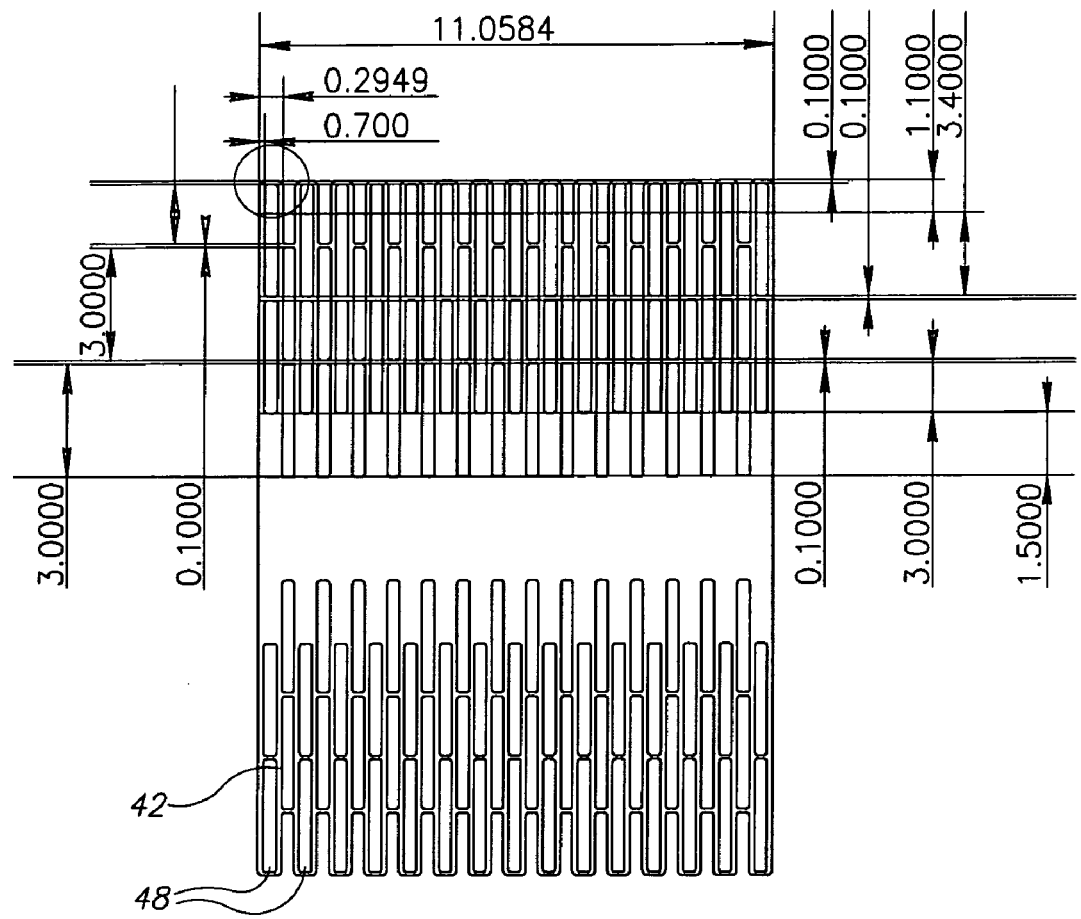
FIGS. 3a–b show the particulars of a construction of an expandable grid for use in constructing the stent depicted in FIGS. 1 and 2.
Figure 3B:
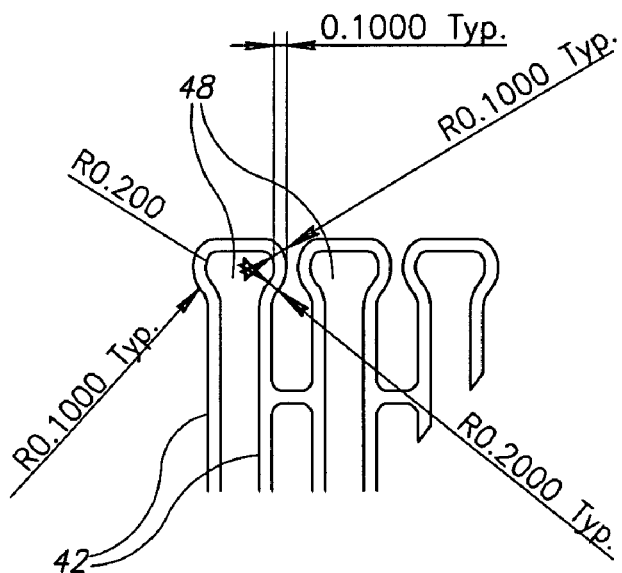

Because the function of stent 20 requires that it be affixed within lumen 28, hollow body 22 may further include at least one expandable portion 36 (two are pictured) so as to fix stent 20 in lumen 28. In order to more firmly affix stent 20 within lumen 28, it is often desirable for hollow body 22 to further include at least two expandable portions 36 as pictured in FIGS. 1, 2, 4, 5 and 6. Stent 20 is often configured so that integrity of expandable portion 36 is preserved during a transition from elasticity to plasticity. Frequently, expandable portion 36 takes the form of a collapsible grid 42 containing a plurality of holes 48. Grid 42 is generally fully contained within a coating 46 (see, FIGS. 4 and 6), for example, a biologically inert coating as described hereinabove. FIGS. 3a–b show an example of details of the construction of a collapsible grid for use as part of stent 20. Stent 20 is depicted in FIG. 2 in an expanded position with expandable portions 36, expanded so that flow passage 30 (indicated by bent arrow) is clearly visible (see also FIG. 6; hollow arrow).

Because the invention was originally conceived to address the problem of ischemic heart disease, lumen 28 is often a coronary sinus and stent 20 is configured for placement therein, so as to decrease a flow of blood therethrough. Decreasing the flow of blood through the coronary sinus, if the decrease is of sufficient magnitude, can cause coronary angiogenesis, thereby eventually reliving cardiac ischemia.

In order to suit stent 20 for use in a coronary sinus as described hereinabove, stent 20 is often constructed with an inner cross sectional dimension 32 of hollow body 22 greater than 7 mm$^2$ and less than 28 mm$^2$. For the same reason, stent 20 is often constructed with a length of hollow body 22, from first end 24 to second end 26, greater than 20 mm and less than 50 mm. These dimensions produce an aspect ratio defined by an inner cross sectional diameter of the hollow body divided by a length of hollow body 22 from first end 24 to second end 26 which is greater than 0.1 and less than 0.2.

According to a preferred embodiment of the present invention a ratio defined by a widest inner cross sectional diameter of said hollow body divided by a narrowest inner cross sectional diameter of said hollow body is greater than 2.6 and less than 4.3.

During use of stent 20, expansion of expandable portions 36 may be achieved, for example, by application of a force which expands expandable portions 36 or by removal of a force which contracts expandable portions 36 as is further explained hereinbelow.

Figure 4:
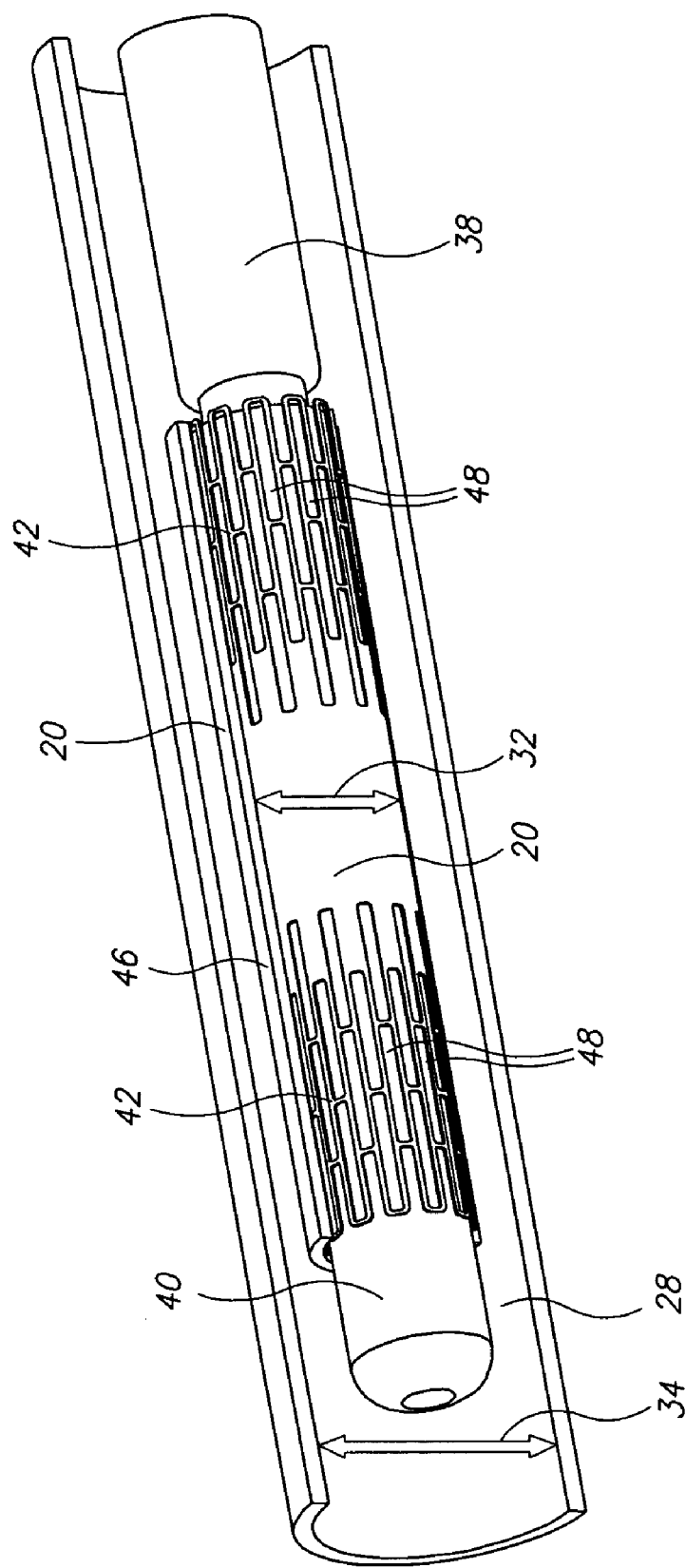
FIG. 4 is a schematic diagram illustrating placement of a stent, the core construction thereof is depicted in FIGS. 1 and 2, in a body lumen by means of a balloon catheter.

The force which expands the expandable portion 36 is suppliable by, for example, an inflatable balloon 40 of a catheter 38 receivable within hollow body 22 of stent 20 (FIG. 4). Catheter 38 may used to implant stent 20 into the body of a patient, for example via the femoral vein, through the superior vena cava and the right atrium to the coronary sinus. Guidance of catheter 38, whether a balloon catheter or any other type of catheter, may be effected under imaging. Imaging may be accomplished, for example, by computer assisted tomography (CT), magnetic resonance imaging (MRI), proton emission tomography (PET), ultrasonography, three dimensional ultrasonography, fluoroscopy, electrophysiological imaging, X-ray imagery or echocardiography. After stent 20 has reached the desired position in lumen 28, the coronary sinus in this example, balloon 40 is inflated, thereby expanding expandable portion 36 and affixing stent 20 within lumen 28. Stent 20 may be fixed in place, for example, as a result of a physical contact 44 between a portion of stent 20 and an inner surface of lumen 28. Alternately, stent may be fixed in place, as a result of a biological process occurring in cells of an inner surface of lumen 28 as a result of a presence therein of stent 20.

Biological processes which would tend to fix stent 20 in place include, but are not limited to, secretion of a fluid, cell death, tissue growth, scarring, clotting, swelling and localized inflammation. After placement of stent 20, balloon 40 is deflated and withdrawn along with catheter 38. The end result of this process is that the effective cross sectional dimension of lumen 28 is reduced from its original size 34 to the size of inner cross sectional dimension 32 of hollow body 22 of stent 20.

Figure 5A:
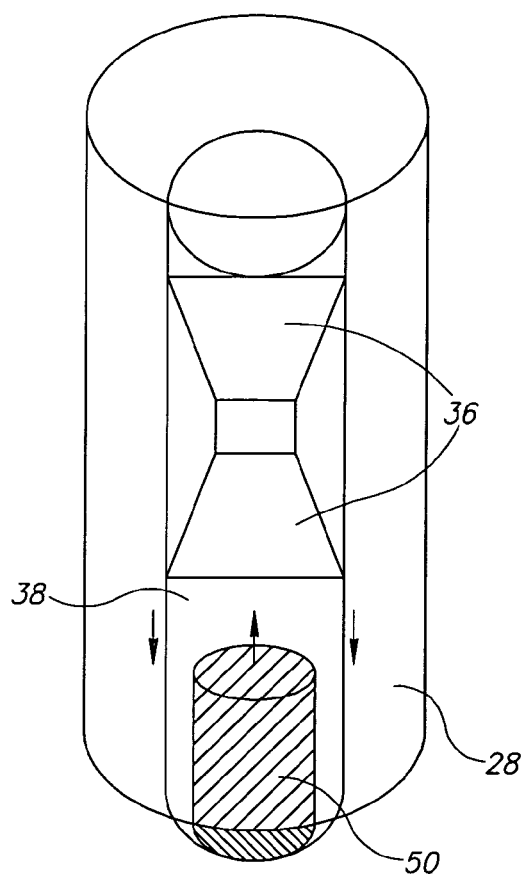
FIGS. 5a–b schematically illustrate an alternate method for placing a stent of the present invention within a body lumen.
Figure 5B:
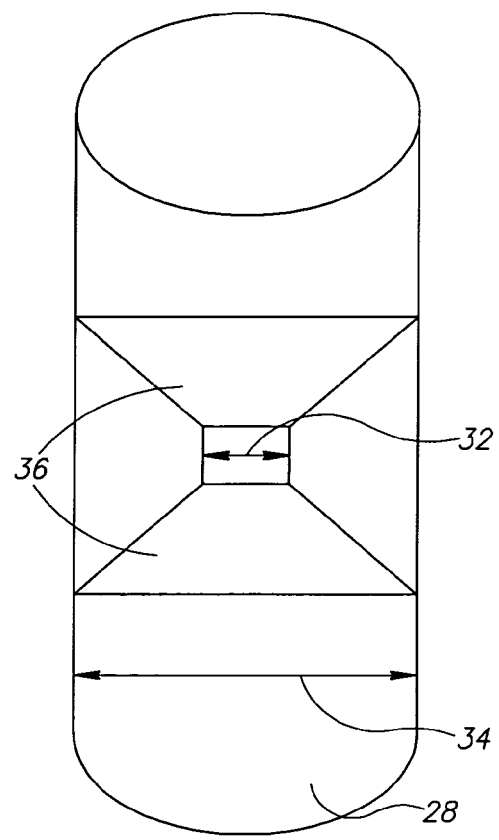

An alternate method of affixing stent 20 in lumen 28 is illustrated in FIGS. 5a–b. This method relies upon removal of a force which contracts expandable portion 36. In contrast to the balloon catheter method described hereinabove, this method employs a catheter 38 equipped with a piston 50. As shown in FIG. 5a, stent 20 is inserted in catheter 38 in a collapsed position. In this case, stent 20 has at least one expandable portion 36 (two are pictured) having an inherent spring-like memory. Insertion and guidance are as described hereinabove for the balloon catheterization method. After stent 20 has reached the desired position in lumen 28, the coronary sinus in this example, piston 50 is translated as indicated by an arrow, while catheter 38 is retracted as indicated by a pair of arrows. Stent 20 is thereby ejected into lumen 28, where expandable portion 36, having an inherent spring-like memory, expands to affix stent 20 within lumen 28 (FIG. 5b). As in the balloon catheterization method, the end result of this process is that the effective cross sectional dimension of lumen 28 is reduced from its original size 34 to the size of inner cross sectional dimension 32 of hollow body 22 of stent 20.

Figure 6:
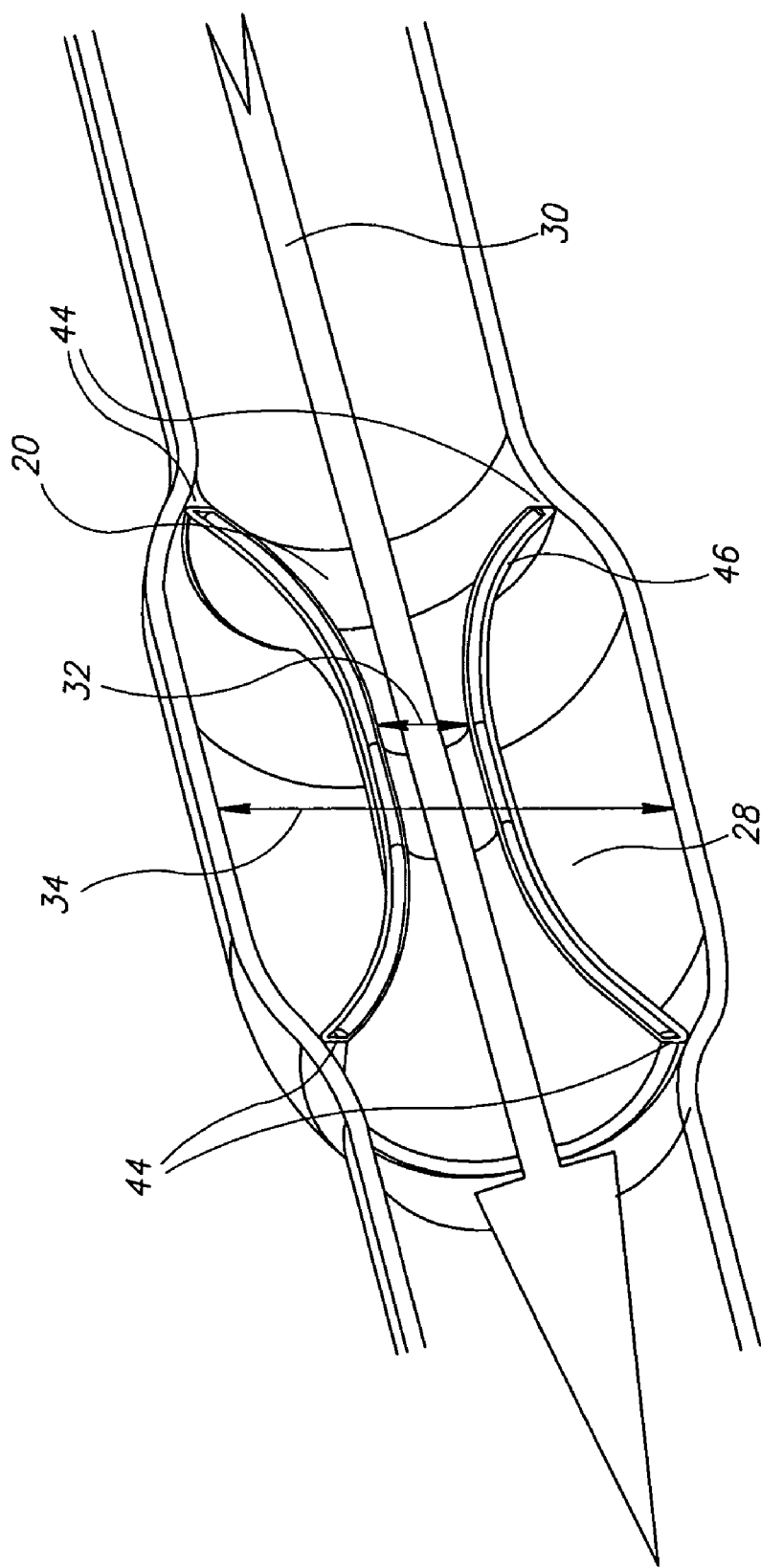
FIG. 6 is a cross sectional view of a stent according to the present invention situated within a body lumen.

As can be seen in FIG. 6, regardless of the method chosen to place stent 20 in lumen 28, a flow passage 30 through lumen 28 is now limited by cross sectional dimension 32 of stent 20 and not by cross sectional dimension 34 of lumen 28. This limitation occurs as a result of contact 44 between stent 20 and lumen 28. Flow through holes 48 of expandable portion 36 is prevented by coating 46 on stent 20.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety. Citation or identification of any reference in this section or in any other section of this application shall not be construed as an admission that such reference is available as prior art to the present invention.

I claim:

1. A flow-reducing intraluminal stent for placement in a coronary sinus of a patient, the stent comprising:
   a hollow central portion having first and second ends and defining a flow passage therethrough; and
   first and second expandable portions located at the first and second ends of the central portion and having respective outer edges,
   wherein the expandable portions are adapted to be expanded within the coronary sinus such that the outer edges widen outward with monotonically increasing diameter to engage a wall of the coronary sinus, so as to firmly affix the stent within the coronary sinus, and
   wherein a diameter of the flow passage is substantially fixed at a size that is predetermined prior to implantation by a structure of the central portion, thus reducing a flow of blood through the coronary sinus.

2. A flow-reducing intraluminal stent for placement in a coronary sinus of a patient, the stent comprising:
   a hollow central portion having first and second ends and defining a flow passage passing therethrough; and
   first and second expandable portions located at the first and second ends of the central portion,
   wherein the expandable portions are adapted to be expanded within the coronary sinus so as to firmly affix the stent within the coronary sinus, while a diameter of the flow passage is substantially fixed at a size that is predetermined prior to implantation by a structure of the central portion, thus reducing a flow of blood through the coronary sinus.

3. The flow-reducing intraluminal stent of claim 2, wherein the stent is constructed of a biologically inert material.

4. The flow-reducing intraluminal stent of claim 3, wherein said biologically inert material is selected from the group consisting of stainless steel, nitinol and biocompatible plastic material.

5. The flow-reducing intraluminal stent of claim 2, wherein the stent is coated with a biologically inert material.

6. The flow-reducing intraluminal stent of claim 5, wherein said biologically inert material is selected from the group consisting of stainless steel, nitinol and biocompatible plastic material.

7. The flow-reducing intraluminal stent of claim 2, wherein the stent is configured to decrease a flow of blood through the coronary sinus.

8. The flow-reducing intraluminal stent of claim 7, wherein said decrease in flow of blood through the coronary sinus is sufficient so as to cause coronary angiogenesis.

9. The flow-reducing intraluminal stent of claim 2, wherein said hollow central portion has an inner cross sectional area greater than 7 $mm^2$.

10. The flow-reducing intraluminal stent of claim 9, wherein said hollow central portion has an inner cross sectional dimension less than 28 $mm^2$.

11. The flow-reducing intraluminal stent of claim 2, wherein said stent has a length greater than 20 mm.

12. The flow-reducing intraluminal stent of claim 11, wherein said stent has a length less than 50 mm.

13. The flow-reducing intraluminal stent of claim 2, wherein a ratio defined by a widest inner cross sectional diameter of said expandable portions, after having been expanded within the coronary sinus, divided by a narrowest inner cross sectional diameter of said hollow central portion is greater than 2.6.

14. The flow-reducing intraluminal stent of claim 13, wherein said ratio is less than 4.3.

15. The flow-reducing intraluminal stent of claim 2, wherein at least one of the expandable portions expands as a result of an occurrence selected from the group consisting of:
   (i) application of a force which expands said at least one of the expandable portions; and
   (ii) removal of a force which contracts said at least one of the expandable portions.

16. The flow-reducing intraluminal stent of claim 15, wherein said force which expands said at least one of the expandable portions is suppliable by an inflatable balloon of a catheter receivable within said stent.

17. The flow reducing intraluminal stent of claim 2, wherein affixing of the flow reducing intraluminal stent in the coronary sinus occurs as a result of a cause selected from the group consisting of:
(i) a physical contact between a portion of the flow reducing intraluminal stent and an inner surface of the coronary sinus; and
ii) a biological process occurring in cells of an inner surface of the coronary sinus as a result of the presence therein of the flow reducing intraluminal stent.

18. The flow reducing intraluminal stent of claim 2, wherein an integrity of said expandable portions is preserved during a transition from elasticity to plasticity.

19. The flow reducing intraluminal stent of claim 2, wherein said expandable portions comprise an expandable grid.

* * * * *